(12) United States Patent
Akaike et al.

(10) Patent No.: US 7,935,814 B2
(45) Date of Patent: May 3, 2011

(54) NITROGUANOSINE-3' 5'-CYCLIC MONOPHOSPHATE COMPOUND AND PROTEIN KINASE G ACTIVATING AGENT

(75) Inventors: Takaaki Akaike, Kumamoto (JP); Teruo Akuta, Tokyo (JP)

(73) Assignee: Kumamoto University, Kumamoto (JP)

( * ) Notice: Subject to any disclaimer, the term of this patent is extended or adjusted under 35 U.S.C. 154(b) by 338 days.

(21) Appl. No.: 11/817,168

(22) PCT Filed: Feb. 28, 2006

(86) PCT No.: PCT/JP2006/303671
§ 371 (c)(1),
(2), (4) Date: Jan. 13, 2009

(87) PCT Pub. No.: WO2006/093110
PCT Pub. Date: Sep. 8, 2006

(65) Prior Publication Data
US 2009/0215716 A1     Aug. 27, 2009

(30) Foreign Application Priority Data
Feb. 28, 2005 (JP) .................. 2005-052649

(51) Int. Cl.
*C07H 19/213* (2006.01)
(52) U.S. Cl. .................. 536/26.12; 536/26.72
(58) Field of Classification Search .......... None
See application file for complete search history.

(56) References Cited

U.S. PATENT DOCUMENTS
6,268,352 B1   7/2001   Song et al.
(Continued)

FOREIGN PATENT DOCUMENTS
JP     2002-523462     7/2002
(Continued)

OTHER PUBLICATIONS (R) PCT-237, PCT/JP2005/303671, English language translation of the International Preliminary Report with cover sheets, mailed on Sep. 20, 2007.*

(Continued)

*Primary Examiner* — Lawrence E Crane
(74) *Attorney, Agent, or Firm* — Greenblum & Bernstein, PLC

(57) ABSTRACT

An object of the present invention is to provide a novel compound that is an agonist of guanosine-3',5'-cyclic monophosphate and has an effect of activating protein kinase G. The present invention provides 8-guanosine-3',5'-cyclic monophosphate compound which is represented by the following formula, and a pharmaceutical composition, especially a protein kinase G activating agent, which contains the 8-guanosine-3',5'-cyclic monophosphate compound as an active ingredient.

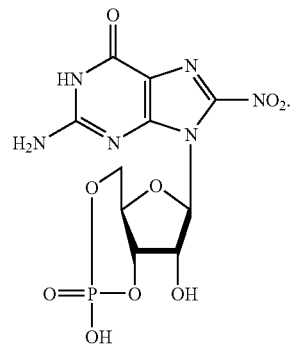

3 Claims, 2 Drawing Sheets

U.S. PATENT DOCUMENTS

2001/0041346 A1 11/2001 Mendelsohn
2004/0087539 A1 5/2004 Du

FOREIGN PATENT DOCUMENTS

| WO | 00/12099 | 3/2000 |
| WO | 01/05837 | 1/2001 |
| WO | 02/062325 | 8/2002 |

OTHER PUBLICATIONS

Sagi, G et al., Synthesis and Enzymatic Activity of Some New Purine Ring System Analogues of Adenosine 3', 5'-Cyclic Monophosphate, Journal of Medicinal Chemistry, 1992, vol. 35, No. 24, pp. 4549-4556.

English language abstract JP 2002-523462, Dec. 3, 2007.

Algara-Suarez et al., "8Br-cGMP mediates relaxation of tracheal smooth muscle through PKA," *Biochemical and Biophysical Research Communications*, vol. 314, No. 2, pp. 597-601, 2004.

Extended European Search Report that issued with respect to European Patent Application No. 06714808.0, mailed Jul. 26, 2010.

International Search Report for PCT/JP2006/303671, mailed Mar. 28, 2006.

* cited by examiner

NITROGUANOSINE-3' 5'-CYCLIC MONOPHOSPHATE COMPOUND AND PROTEIN KINASE G ACTIVATING AGENT

CROSS-REFERENCE TO RELATED APPLICATIONS

The present application is a U.S. national stage application of PCT/JP2006/303671, filed Feb. 28, 2006.

TECHNICAL FIELD

The present invention relates to a novel 8-nitroguanosine-3',5'-cyclic monophosphate compound that is an agonist of guanosine-3',5'-cyclic monophosphate and has an effect of activating a guanosine-3',5'-cyclic monophosphate-dependent protein phosphorylation enzyme (protein kinase G), and a pharmaceutical composition containing the compound as an active ingredient. The present invention particularly relates to a protein kinase G activating agent.

BACKGROUND ART

Guanosine-3',5'-cyclic monophosphate (cGMP) is an intracellular signaling molecule that transmits signals such as nitric oxide (NO) and natriuretic peptides that enter cells coming from the outside thereof. Examples of receptor proteins of cGMP known to date include a cGMP-dependent protein phosphorylation enzyme (protein kinase G), a cGMP control channel, and a cGMP-degrading enzyme (phosphodiesterase, PDE). In particular, the initial reaction for signaling mediated by cGMP is thought to be activation of protein kinase G. Protein kinase G is a serine/threonine phosphorylation enzyme, and is activated at a cGMP concentration of around μM. Regarding vascular smooth muscle cells, it is thought that protein kinase G phosphorylates several portions including serine (Ser) at position 695 of MBS (myosin-binding subunit) that composes MLCP (myosin light chain phosphatase) so that vascular smooth muscle cells are relaxed. Furthermore, protein kinase G phosphorylates Ser 683 and Ser 696 (bovine type) of an inositol trisphosphate ($IP_3$) receptor-associated cGKI substrate (IRAG) existing in the endoplasmic reticulum, thereby inhibiting the release of Ca (induced by $IP_3$) from the endoplasmic reticulum. In addition to this, it is known that the Ca-dependent K channel, ATP-sensitive K channel, and L-, N-, and T-type channels are activated by phosphorylation. Phosphorylation of the Ca channel at the nerve endings is thought to promote the release of neurotransmitters. PDE5 activity is also regulated by protein kinase G such that cGMP is degraded to GMP by the PDE5 activated via phosphorylation of PDE5 at Ser92 (human type) induced by protein kinase G.

Hence, a drug that activates protein kinase G is useful as a therapeutic drug for hypertension, pulmonary hypertension, angina pectoris, arteriosclerotic cardiovascular diseases, erectile dysfunction, and the like. Examples of known compounds that activate protein kinase G include:
8-bromoguanosine-3',5'-cyclic monophosphate (8-Br-cGMP), 8-bromoguanosine-3',5'-cyclic monophosphorothioate, Sp-isomer (Sp-8-Br-cGMPS), 8-(4-chlorophenylthio)guanosine-3',5'-cyclic monophosphate (8-pCPT-cGMP), 8-(4-chlorophenylthio)guanosine-3',5'-cyclic monophosphate, acetoxymethyl ester (8-pCPT-cGMP-AM), 8-(4-chlorophenylthio)guanosine-3',5'-cyclic monophosphorothioate, Sp-isomer (Sp-8-pCPT-cGMPS), 8-(4-chlorophenylthio)-β-phenyl-1,$N^2$-ethenoguanosine-3',5'-cyclic monophosphate (8-pCPT-PET-cGMP), 8-(4-chlorophenylthio)-β-phenyl-1,$N^2$-ethenoguanosine-3',5'-cyclic monophosphorothioate, Sp-isomer (Sp-8-pCPT-PET-cGMPS), guanosine-3',5'-cyclic monophosphorothioate, Sp-isomer (Sp-cGMPS), 8-bromo-β-phenyl-1,N2-ethenoguanosine-3',5'-cyclic monophosphorothioate, Sp-isomer (Sp-8-Br-PET-cGMPS), 1-aminoguanosine-3',5'-cyclic monophosphate (1-$NH_2$-cGMP), and 8-(2-aminophenylthio)guanosine-3',5'-cyclic monophosphate (8-APT-cGMP). cGMP agonists are generally used as research reagents for the analysis of intracellular signaling mechanism mediated by cGMP. In particular, 8-Br-cGMP is frequently used and is known to have not only an in vitro effect in a culture cell system, but also in an in vivo vasodilator effect (*Eur J Pharmacol.* 118, 155-161 (1985)).

Moreover, organic nitrate preparations such as nitroglycerin which activate soluble guanylate cyclase, sildenafil which specifically inhibits PDE5 (which is a cGMP-degrading enzyme), and the like, also have an effect of elevating intracellular cGMP concentration. They all exert their pharmacological effects by indirectly activating protein kinase G and have already been clinically used as pharmaceutical products for treating hypertension, angina pectoris, erectile dysfunction, and the like.

DISCLOSURE OF THE INVENTION

Object to be Solved by the Invention

An object to be solved by the present invention is to provide a novel compound that is an agonist of cGMP and has an effect of activating protein kinase G.

Means for Solving the Object

As a result of intensive studies to discover novel compounds of guanosine derivatives generated through reaction of nucleic acids with reactive nitrogen oxide species, the present inventors have discovered that an 8-nitroguanosine-3',5'-cyclic monophosphate compound passes through the cell membrane and activates protein kinase G within the cell, so as to conduct intracellular signaling. Thus, the present inventors have completed the present invention.

Specifically, according to the present invention, an 8-nitroguanosine-3',5'-cyclic monophosphate compound represented by the following formula or a salt thereof, a hydrate, or a solvate thereof is provided.

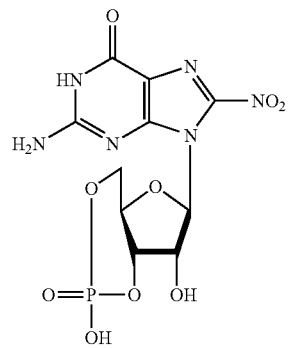

According to another aspect of the present invention, a pharmaceutical composition which comprises the above 8-nitroguanosine-3',5'-cyclic monophosphate compound or a salt thereof, a hydrate thereof, or a solvate thereof as an active ingredient is provided. Preferably, the pharmaceutical composition of the present invention is a therapeutic agent for hypertension, a therapeutic agent for angina pectoris, or a therapeutic agent for erectile dysfunction. Preferably, the pharmaceutical composition of the present invention improves conditions affected by hypertension, angina pectoris, or erectile dysfunction through activation of protein kinase G.

According to still another aspect of the present invention, a protein kinase G activating agent which comprises the above 8-nitroguanosine-3',5'-cyclic monophosphate compound or a salt thereof, a hydrate thereof, or a solvate thereof as an active ingredient is provided.

According to still another aspect of the present invention, a method for producing an 8-nitroguanosine-3',5'-cyclic monophosphate compound is provided, which comprises causing the following compound 1:

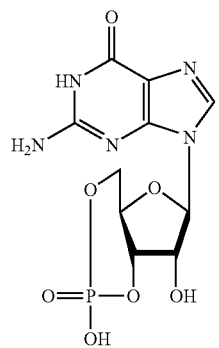

1 to react with bromine so as to produce the following compound 2:

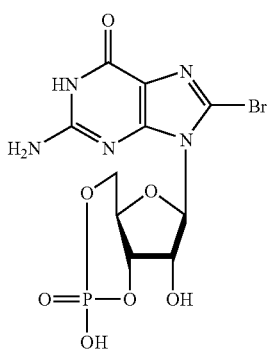

2 and then causing the above compound 2 to react with nitrous acid so as to produce the following compound 3:

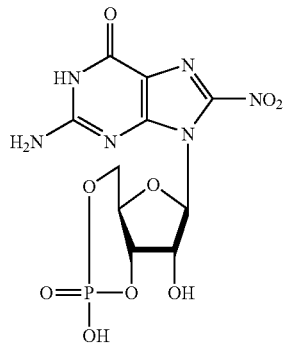

3

According to still another aspect of the present invention, a method for treating diseases associated with protein kinase G activity (e.g., hypertension, angina pectoris, erectile dysfunction, or the like) is provided, which comprises administering the above 8-nitroguanosine-3',5'-cyclic monophosphate compound or a salt thereof, or a hydrate thereof, or a solvate thereof to mammals including humans.

According to still another aspect of the present invention, a method for activating protein kinase G is provided, which comprises administering the above 8-nitroguanosine-3',5'-cyclic monophosphate compound or a salt thereof, a hydrate thereof, or a solvate thereof to mammals including humans.

According to still another aspect of the present invention, the use of the above 8-nitroguanosine-3',5'-cyclic monophosphate compound or a salt thereof, a hydrate thereof, or a solvate thereof is provided for producing a pharmaceutical composition (particularly, a pharmaceutical composition for treating and/or preventing diseases associated with protein kinase G activity, such as hypertension, angina pectoris, and erectile dysfunction) or a protein kinase G activating agent.

PREFERRED EMBODIMENTS OF THE INVENTION

The compound of the present invention is represented by the following formula, wherein a nitro group is bound to position 8.

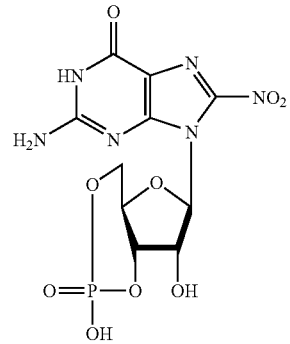

The compound of the present invention may be in any forms including free forms, forms of salt, forms of hydrate (including a hydrate salt), or forms of solvate. Examples of such salt forms include an inorganic acid salt such as hydrochloride, nitrate, or sulfate, an organic acid salt such as acetate, citrate, propionate, butyrate, formate, lactate, or succinate, and an ammonium salt. In particular, a pharmaceutically acceptable salt is preferable. The type of organic solvent that forms a solvate is not particularly limited. Examples of such organic solvent include methanol, ethanol, ether, dioxane, and tetrahydrofuran.

Next, a method for synthesizing the compound of the present invention is as described below. The compound of the present invention, which is represented by the above formula, can be synthesized according to the following flow chart, for example.

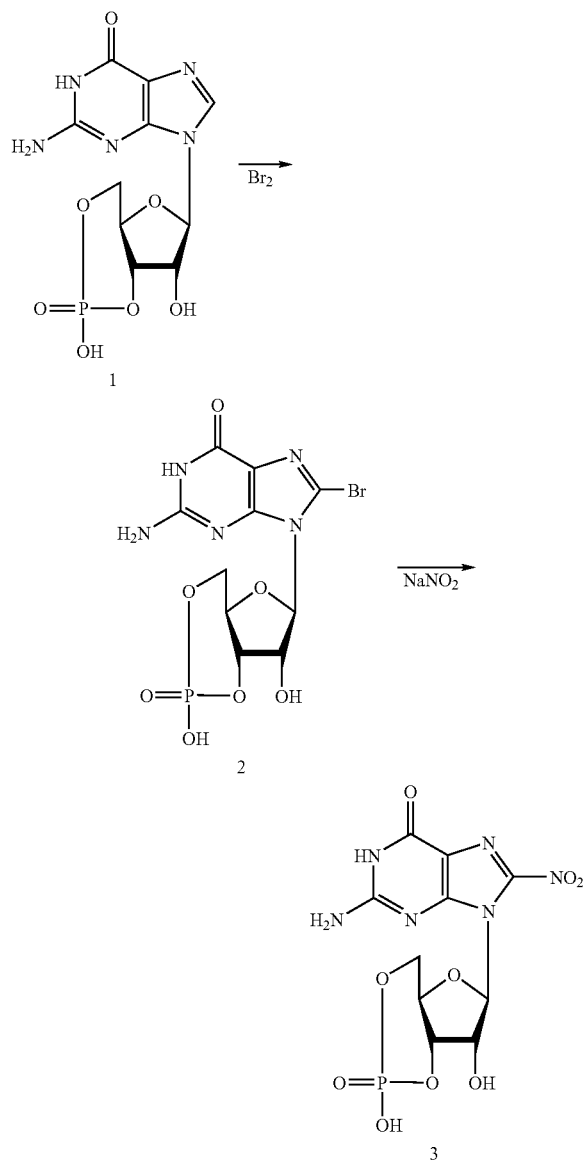

In the above flow chart, a compound (1) that is a starting material can be easily synthesized by reacting a N-benzoylguanosine-5' phosphate monohydrate calcium salt, which is a known compound, with 4-morpholine-N,N'-dicyclohexylcarboxamidine in pyridine at 100° C. for several hours (*J. Am. Chem. Soc.*, 83, 698-706, 1961). In addition, the N-benzoylguanosine-5' phosphate monohydrate calcium salt as a raw material is slightly soluble in a solvent. Hence, salt exchange is performed with carboxamidin. Thus the N-benzoylguanosine-5' phosphate monohydrate calcium salt becomes easily soluble in a solvent and can also be condensed using N,N'-dicyclohexylcarbodiimide (DCC) (condensation agent).

The thus prepared compound (1) is reacted with bromine in a solvent such as formamide on ice for approximately 0.5 hours to obtain a compound (2). The compound (2) is reacted with sodium nitrite at 70° C. for approximately 5 days such that it becomes possible to obtain a compound (3). For isolation and purification of the compound of the present invention and synthetic intermediates, general means for isolation and purification of organic compounds may be employed. For example such isolation and purification can be performed using re-crystallization, various types of chromatography, or the like.

Regarding the use of the compound of the present invention, the compound is useful as an agonist of cGMP. The compound is also useful as a therapeutic agent for diseases (e.g., hypertension, angina pectoris, and erectile dysfunction) that can be treated by activating protein kinase G to undergo intracellular signaling.

Regarding hypertension, excessive vascular contraction is thought to be a factor that elevates blood pressure. Prolonged hypertension damages blood vessels, inducing complications such as heart disease (e.g., angina pectoris and myocardial infarction), cerebrovascular disorder (e.g., encephalorrhagy and brain infarction), kidney failure, aortic aneurysm (a disease characterized by bulge formation in the walls of aortic arteries and aneurysms that may rupture), retinopathy (e.g., fundal hemorrhage), and arteriosclerosis. As described above in the Description, it is thought that vascular smooth muscle cells are relaxed when protein kinase G phosphorylates several positions including Ser695 of MBS (myosin-binding subunit) that composes MLCP (myosin light chain phosphatase). The 8-nitroguanosine-3',5'-cyclic monophosphate compound of the present invention is useful as a therapeutic agent for hypertension, since the compound has an effect of relaxing vascular smooth muscle through activation of protein kinase G.

Angina pectoris occurs when oxygen supply cannot keep up with the oxygen demand in cardiac muscle because of circulatory deficits generated in the coronary arteries due to thrombus, vasoconstriction, or the like. Of such pathological conditions, ischemia (oxygen deficiency) occurs transiently and the damage to the cardiac muscle is reversible. A drug capable of relaxing vascular smooth muscle and extending blood vessels (and particularly, veins) can reduce the preload of the cardiac muscle, can reduce cardiac work as a result, and thus can reduce oxygen demand. Thus, such drug is useful as a therapeutic drug for angina pectoris. The 8-nitroguanosine-3',5'-cyclic monophosphate compound of the present invention is useful as a therapeutic agent for angina pectoris, since the compound has an effect of relaxing vascular smooth muscle through activation of protein kinase G.

Erectile dysfunction is mainly induced as described below. The level of NO secreted from the vascular endothelium is lowered. The level of NO secreted from the pudendal nerve ending by nerve stimulation from the central nerve is also lowered. The resulting lower level of guanylate cyclase enzyme activity in vascular smooth muscle causes a decrease in the production level of cGMP. The resulting lowered level of protein kinase G activity causes an increase in the inflow of Ca ions into cells. As a result, the vascular smooth muscle relaxing reaction does not occur, or such relaxing reaction does not last long, even in the case of stimulation because of sexual need. The 8-nitroguanosine-3',5'-cyclic monophosphate compound of the present invention has an effect of activating protein kinase G, and thus is useful as a therapeutic agent for erectile dysfunction.

The compound of the present invention can be administered to a human for treating the above diseases via any route, including oral administration, enteral administration, parenteral administration, and local administration. The dose of the compound is adequately determined depending on patient age, pathological conditions, body weight, and the like. In general, the dose is selected from a range between 0.1 mg/kg and 1000 mg/kg body weight per day and is administered once or administered in divided doses.

For the formulation of the compound of the present invention, the compound is generally used as a composition which contains a generally used carrier for formulation, excipient, and other additives. Examples of carriers include solid carriers such as lactose, kaolin, sucrose, crystalline cellulose, corn starch, talc, agar, pectin, stearic acid, magnesium stearate, lecithin, and sodium chloride, and liquid carriers such as glycerin, peanut oil, polyvinylpyrrolidone, olive oil, ethanol, benzyl alcohol, propylene glycol, and water. Any dosage form can be employed. When a solid carrier is used, examples of a dosage form include tablets, powdered drugs, fine granules, encapsulated formulations, suppositories, and troches. When a liquid carrier is used, examples of a dosage form include syrups, emulsions, soft gelatin capsules, creams, gels, pastes, and injections.

The present invention is described in greater detail with reference to the following examples (synthesis example and test examples), although the present invention is not limited to these examples.

EXAMPLES

Synthesis Example

8-Nitroguanosine-3',5'-cyclic monophosphate was synthesized by a partially modified version of the method of Kapuler, A. M et al. (*Biochemistry* 10, 4050-4061, 1971). Specifically, 8-Br-cGMP was synthesized by a bromination reaction using cGMP as a starting material in the $1^{st}$ step. Subsequently in the $2^{nd}$ step, 8-nitroguanosine-3',5'-cyclic monophosphate was synthesized by a nitration reaction. Wako guaranteed reagents were used as an organic solvent reagent (except in special cases). cGMP (compound (1), 150 mg, produced by MP Biomedicals) was dissolved in 5 ml of formamide, and 500 µl of bromine was added to the solution on ice. Thus bromination was performed via 30 minutes of reaction. Two ml of aniline was added to the solution to terminate the reaction. Subsequently, diethylether was added in an amount 3 times greater than the reaction volume so as to remove aniline via extraction of aniline into the upper (ether) layer. Extraction was repeated 3 times, so that aniline was completely removed. Subsequently, 1N NaOH was added to a formamide layer and then the layer was adjusted to pH 9.0. Butanol (20 ml) and pure water (5 ml) were added. The resultant solution was stirred well and then 8-Br-cGMP was recovered in the lower (aqueous) layer. The recovered 8-Br-cGMP was condensed using a rotary evaporator and then allowed to stand overnight at 4° C. The precipitate (8-Br-cGMP) was recovered by centrifugation (15,000 rpm, 30 min, 4° C.), and 4 ml of pure water was added thereto again and the precipitate was dissolved. The resultant was filtered using a 0.45-µm filter. 8-Br-cGMP was purified by reverse-phase chromatography (mobile phase: 0.02% trifluoroacetic acid, 20% methanol, and flow rate of 3.5 ml/min) using TSKgel ODS-80Ts (21.5×300 mm) (produced by Tosoh Corporation). 100 ml of a peak fraction taken during a retention time of approximately 30 minutes (between 35 minutes to 65 minutes) was collected. The fraction was then condensed to 1 ml using a rotary evaporator. The resultant was freeze-dried so that 53.4 mg (yield: 35.6%) of compound (2) in the form of powder was obtained.

The powdery compound (2) was dissolved in dimethylsulfoxide at a final concentration of 83 mM. 5 N hydrochloric acid was added to the solution at a final concentration of 34.5 mM. Immediately after the addition, 1 M sodium nitrite dissolved in dimethylsulfoxide was added at a final concentration of 333 mM. Reaction was performed for 5 days at 70° C., so that the nitration reaction was performed. After the completion of the reaction, pure water was added in a volume 2.3 times greater than that of the reaction solution. The solution was adjusted at pH 8.5-9.0 using 1N NaOH. 1-Butanol was added to the solution to double the volume of the solution and then the solution was stirred. The thus obtained aqueous layer was condensed using a rotary evaporator.

The condensed sample was filtered using a 0.45-µm filter. High-purity 8-nitroguanosine-3',5'-cyclic monophosphate was obtained through 3 instances of reverse-phase chromatography using TSK-gel ODS-80Ts (21.5×300 mm) performed under different mobile phase conditions. The $1^{st}$ instance of reverse-phase chromatography was performed using a mobile phase (10 mM sodium phosphate buffer (pH7.0) and 16% methanol) at a flow rate of 3.5 ml/min and then a peak fraction taken during a retention time of approximately 3 minutes (between 55 and 58 minutes) was recovered. The fraction was condensed using a rotary evaporator and then 100% ethanol cooled at −20° C. was added, so that the precipitated salt was removed by centrifugation. Ethanol (100%) was added again to the thus recovered ethanol supernatant and then the resultant was centrifuged, so that an ethanol layer was recovered. Ethanol was removed in a gas phase using a rotary evaporator via heating and condensation. An aqueous solution of 8-nitroguanosine-3',5'-cyclic monophosphate was recovered. The $2^{nd}$ instance of reverse-phase chromatography was performed using a mobile phase (10 mM sodium phosphate buffer (pH 7.0), 100 mM NaCl, and 16% methanol) at a flow rate of 3.5 ml/min and then a peak fraction taken during a retention time of approximately 8 minutes (between 59 and 67 minutes) was recovered. The fraction was condensed using a rotary evaporator and then the resultant was subjected to desalting using ethanol. The $3^{rd}$ instance of reverse phase chromatography was performed using a mobile phase (0.02% trifluoroacetic acid and 20% methanol) at a flow rate of 3.5 ml/min and then a peak fraction taken during a retention time of approximately 15 minutes (between 50 and 65 minutes) was recovered. The fraction was condensed using a rotary evaporator. The resultant was freeze-dried so that 11.1 mg (yield: 20.8%) of compound (3) in the form of powder was obtained.

The thus obtained powdery compound (3) was dissolved in pure water added thereto. The solution was subjected to mass spectroscopy using LC-MS (LCMS-QP8000α) (SHIMADZU). As a result, an [M+H]⁺390 peak was detected in agreement with a peak fraction taken during the retention time between 15 and 18 minutes. Specifically, the results agreed with the theoretical values.

¹H NMR and spectrum data such as that regarding MS and UV spectra of the thus obtained compound (3), are as shown below.

¹H NMR (400 MHz, DMSO-$d_6$): δ: 4.06 (1H, ddd, J=4.9, 10, 10 Hz), 4.28 (1H, ddd, J=1.7, 10, 10 Hz), 4.43 (1H, ddd, J=20, 10, 4.9 Hz), 4.83 (1H, d, J=5.4 Hz), 5.02 (1H, ddd, J=10, 5.4, 1.7 Hz), 6.00 (1H, br s), 6.33 (1H, s), 7.05 (2H, br s), 11.3 (1H, s)

MS (ESI, negative):

| | |
|---|---|
| Calculated for $C_{10}H_{11}N_6O_9P$ ([M – H]$^-$): | 389.02 |
| Found: | 389.10 |
| UV spectrum: $\lambda_{max}$ = 253, 275, 390 nm (solvent: $CH_3OH$) | |

Test Example 1

Effect of Activating Protein Kinase G

Intracellular signaling conducted by 8-nitroguanosine-3',5'-cyclic monophosphate through mediation of protein kinase G was analyzed according to the method of Sergei D. Rybalkin et al (*J. Biol. Chem.* 277 3310-3317, 2002). Specifically, phosphorylation of Ser at position 157 of VASP (Vasodilator Stimulated Phosphoprotein), a substrate protein of protein kinase G, was detected by Western blotting. Specifically, human uterine smooth muscle cells (produced by CAMBREX) were cultured in Dulbecco's Modified Eagle Medium (DMEM-10% FCS) containing 10% fetal calf serum (FCS). The cells were seeded on a 6-well plate (produced by Falcon) at $4\times10^5$ cells/well and then cultured for 24 hours. The resultant was washed 3 times using phosphate buffered saline (PBS). Subsequently, DMEM-10% FCS containing 1 mM 8-nitroguanosine-3',5'-cyclic monophosphate and 1 mM 8-Br-cGMP (produced by SIGMA) was added to the cells. Medium was immediately removed at 5 minutes, 10 minutes, 15 minutes, and 30 minutes after addition, followed by 2 instances of washing with PBS. A cell lysis solution (20 mM Tris-HCl (pH 8.0), 0.15 M NaCl, 1 mM EDTA, 1 mM EGTA, 1% TritonX-100, 2.5 mM sodium pyrophosphate, 1 mM β-glycerolphosphate, nM $Na_3VO_4$, 1 μg/ml leupeptin, and 1 mM PMSF) was added. The resultant was allowed to stand on ice for 5 minutes, recovered using a cell scraper, transferred into an Eppendorf tube, and then ultrasonicated twice (5 seconds each). Thus, the cells were sufficiently disrupted. The disrupted cells were centrifuged (15,000 rpm, 10 minutes, and 4° C.). The protein concentration of the soluble fraction of the supernatant was determined using a BCA protein assay (produced by PIERCE). The fraction was subjected to 10% SDS-polyacrylamide gel electrophoresis at 10 μg (of the protein of the soluble fraction)/lane. The resultant was blotted on a PVDF membrane (produced by Millipore) using a semi-dry blotting apparatus. The resultant was subjected to blocking using TBST (20 mM Tris-HCl (pH7.6), 137 mM NaCl, and 0.1% Tween 20) containing 5% (w/v) skim milk (produced by Difco). An anti-VASP (Ser$^{157}$) mouse monoclonal antibody (produced by Alexis Biochemicals) as a primary antibody was diluted 1000-fold in TBST containing 5% (w/v) skim milk, followed by overnight reaction at 4° C. A horseradish-peroxidase-labeled anti-mouse goat antibody (produced by Amersham Biosciences) as a secondary antibody was diluted 1000-fold in TBST containing 5% (w/v) skim milk, followed by 1 hour of reaction at room temperature. The resultant was then washed 3 times with TBST (10 minutes each), chemiluminescence was detected using LAS 1000plus (produced by FujiFilm) and ECL-plus (produced by Amersham Biosciences) as color developers, and then image files were incorporated. Subsequently, the PVDF membrane was treated with a reprobing buffer (62.5 mM Tris-HCl (pH 6.7), 2% SDS, and 100 mM 2-mercaptoethanol) added thereto at 50° C. for 30 minutes, thereby removing antibodies from the membrane. Blocking was performed again using TBST containing 5% (w/v) skim milk. An anti-VASP rabbit polyclonal antibody (produced by Alexis Biochemicals) as a primary antibody was diluted 1000-fold with TBST containing 5% (w/v) skim milk and then caused to react overnight at 4° C. A horseradish peroxidase-labeled anti-rabbit goat antibody (produced by Amersham Biosciences) as a secondary antibody was diluted 1000-fold with TBST containing 5% (w/v) skim milk, followed by a one-hour reaction at room temperature. Subsequently, images were incorporated with LAS in a manner similar to that above. FIG. 1 shows the results. As is understood from the results in FIG. 1, no bands were detected at 0 minutes, but a 50-kDa band of VASP having the phosphorylated Ser at position 157 was detected at 5, 10, 15, and 30 minutes after addition of 8-nitroguanosine-3',5'-cyclic monophosphate or 8-Br-cGMP. Furthermore, as a result of using an antibody that recognizes the entire VASP molecule, a thick 47-kDa band of non-phosphorylated VASP protein was observed at 0 minutes and almost no 50-kDa band was detected, but a thick 50-kDa band that had shifted to the higher molecular weight side because of phosphorylation was detected in all cases at 5 minutes or more after the addition of 8-nitroguanosine-3',5'-cyclic monophosphate. Specifically, it was demonstrated that 8-nitroguanosine-3',5'-cyclic monophosphate carries out signaling mediated by protein kinase G in a manner similar to cGMP.

Test Example 2

Effect of Relaxing Vascular Smooth Muscle

The effect of relaxing vascular smooth muscle exerted by 8-nitroguanosine-3',5'-cyclic monophosphate was determined according to the method of Magnus R (*Ergen Physiol.* 2, 637-672, 1903) by causing phenylephrine, which is an $\alpha_1$ adrenergic receptor agonist, to act to cause pre-contraction of an excised rat carotid artery ring specimen, adding 8-nitroguanosine-3',5'-cyclic monophosphate at different concentrations, and then determining the resulting relaxing effect using Magnus laboratory equipment, Specifically, an SD rat (male, 10-week-old, body weight of 350 g, CHARLES RIVER LABORATORIES JAPAN, INC.) was sacrificed under ether anesthesia, a carotid artery was excised, a stainless-steel bar was inserted into the intravascular lumen, and then endothelial cells were removed through scraping, thereby preparing ring vascular specimens of approximately 4 mm each. The vascular specimens were immersed in 3 ml of a Krebs buffer (1.2 mM $NaHPO_4$, 120 mM NaCl, 5.9 mM KCl, 2.5 mM $CaCl_2$, 1.2 mM $MgCl_2$, 15.5 mM $NaHCO_3$, and 11.5 mM glucose). The Krebs buffer used herein had been previously kept at 37° C., aerated with 95% $O_2$+5% $CO_2$ for oxygenation, and adjusted to pH of 7.4. The ring vascular specimens were fixed within a microtissue organ bath MTOB-2 (produced by Labo Support Co., Ltd.). Isometric tension was measured at the resting tension of 1 g using an isometric transducer and an amplifier for such transducer (AG-621G Nihon Kohden Corporation). A PowerLab data acquisition apparatus (AD instruments) was used for data analysis. 1-Phenylephrine hydrochloride (produced by Wako Pure Chemical Industries, Ltd.) was added at a final concentration of 100 nM to the Krebs buffer, so as to sufficiently contract the blood vessels. 8-Nitroguanosine-3',5'-cyclic monophosphate and 8-Br-cGMP were each cumulatively administered at final concentrations of 1 μM, 3 μM, 10 μM, 30 μM, 100 μM, and 300 μM. The relaxing action on vascular smooth muscle was determined. FIG. 2 shows the results. As is understood from the results in FIG. 2, 8-nitroguanosine-3', 5'-cyclic monophosphate exerted a relaxing effect on a blood vessel derived from the rat carotid artery that had been contracted using phenylephrine. In particular, whereas the 8-nitroguanosine-3',5'-cyclic monophosphate concentration required for exertion of the tension variation of 0.1 g was 10 μM, the 8-Br-cGMP concentration required for the same was 30 μM. Thus, it was demonstrated that 8-nitroguanosine-3', 5'-cyclic monophosphate exerts the effect of relaxing vascular smooth muscle at a level approximately 3 times greater than that of 8-Br-cGMP.

INDUSTRIAL APPLICABILITY

The compound of the present invention has the effect of activating protein kinase G and is useful as a therapeutic agent for hypertension, angina pectoris, erectile dysfunction, and the like.

Figure 1:
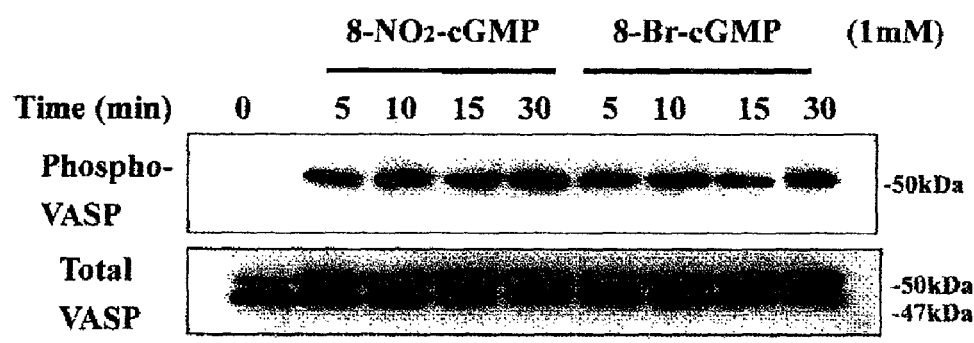
FIG. 1 shows the activation of protein kinase G by the 8-nitroguanosine-3',5'-cyclic monophosphate of the present invention, as analyzed by Western blotting.
Figure 2:
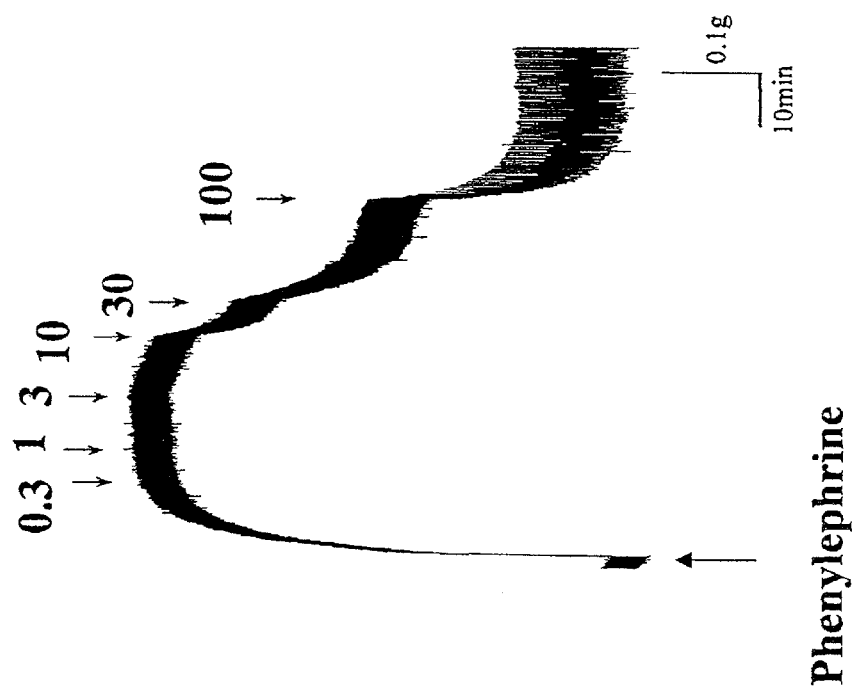
FIG. 2 shows the blood vessel relaxation effect of 8-nitroguanosine-3',5'-cyclic monophosphate of the present invention, as analyzed.
Figure 2:
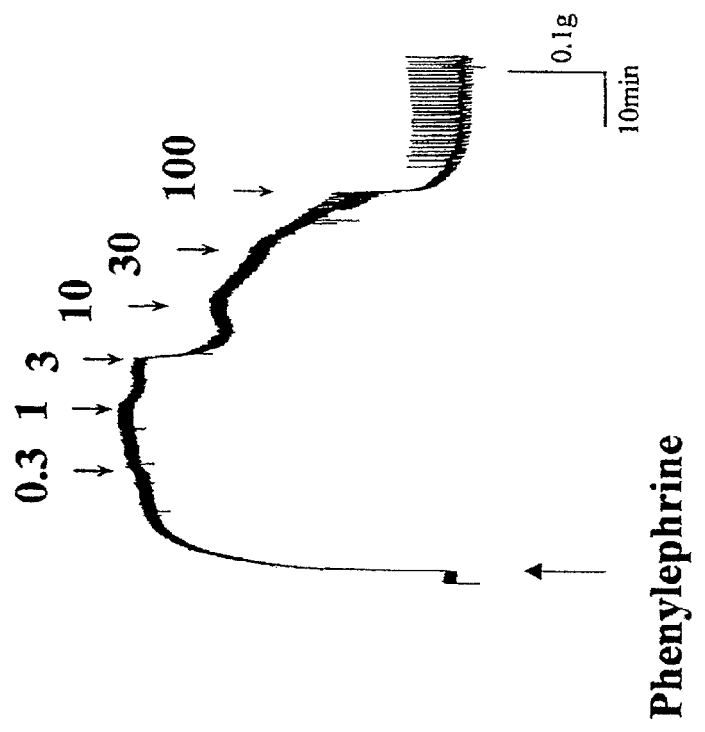

The invention claimed is:

1. An 8-nitroguanosine-3',5'-cyclic monophosphate compound represented by the following structure

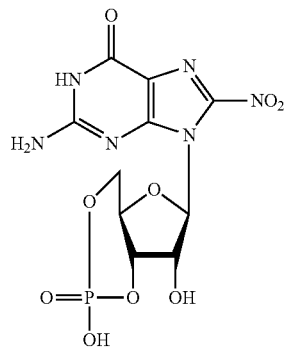

and pharmaceutically acceptable salts and hydrates thereof.

2. A pharmaceutical composition which comprises the 8-nitroguanosine-3',5'-cyclic monophosphate compound of claim 1 or a pharmaceutically acceptable salt or hydrate thereof as an active ingredient in combination with a pharmaceutically acceptable carrier.

3. A method for producing an 8-nitroguanosine-3',5'-cyclic monophosphate compound of claim 1, which comprises causing the compound represented by formula 1:

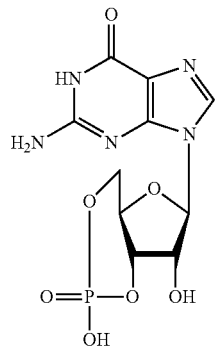

formula 1 to react with bromine so as to produce the compound represented by formula 2:

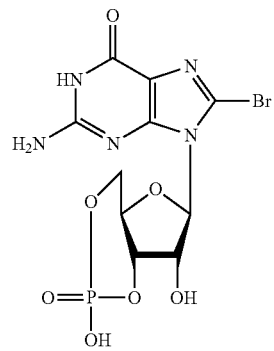

formula 2 and then causing the above compound 2 to react with nitrous acid so as to produce the compound represented by formula 3:

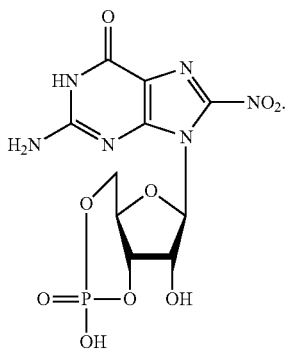

formula 3

* * * * *